United States Patent
Pinkos et al.

(10) Patent No.: US 9,809,517 B2
(45) Date of Patent: Nov. 7, 2017

(54) METHOD FOR BREAKDOWN OF FORMATES

(71) Applicant: BASF SE, Ludwigshafen (DE)

(72) Inventors: Rolf Pinkos, Bad Duerkheim (DE);
Nicolas Marion, Mannheim (DE);
Helmut Kronemayer, Dossenheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/124,944

(22) PCT Filed: Mar. 5, 2015

(86) PCT No.: PCT/EP2015/054619
§ 371 (c)(1),
(2) Date: Sep. 9, 2016

(87) PCT Pub. No.: WO2015/135830
PCT Pub. Date: Sep. 17, 2015

(65) Prior Publication Data
US 2017/0015608 A1    Jan. 19, 2017

(30) Foreign Application Priority Data

Mar. 12, 2014 (EP) ..................................... 14159198

(51) Int. Cl.
*C07C 29/90* (2006.01)
*C07C 29/141* (2006.01)

(52) U.S. Cl.
CPC ............ *C07C 29/141* (2013.01); *C07C 29/90* (2013.01)

(58) Field of Classification Search
CPC .............................. C07C 29/141; C07C 29/90

USPC ......................................................... 568/445
See application file for complete search history.

(56) References Cited

U.S. PATENT DOCUMENTS

| | | |
|---|---|---|
| 6,187,971 B1 | 2/2001 | Kratz et al. |
| 6,201,160 B1 | 3/2001 | Brudermüller et al. |
| 7,439,406 B2 | 10/2008 | Wartini et al. |
| 9,132,417 B2 | 9/2015 | Tompers et al. |
| 2008/0207953 A1 | 8/2008 | Houssin et al. |

FOREIGN PATENT DOCUMENTS

| | | |
|---|---|---|
| CN | 103449970 A | 12/2013 |
| WO | WO-9532171 A1 | 11/1995 |
| WO | WO-9828253 A1 | 7/1998 |
| WO | WO-2004092097 A1 | 10/2004 |
| WO | WO-2007006719 A1 | 1/2007 |
| WO | WO-2011061185 A2 | 5/2011 |
| WO | WO-2011141470 A1 | 11/2011 |

OTHER PUBLICATIONS

International Search Report for PCT/EP2015/054619 dated Jun. 1, 2015.
Written Opinion of the International Searching Authority for PCT/EP2015/054619 dated Sep. 17, 2015.

*Primary Examiner* — Sikarl Witherspoon
(74) *Attorney, Agent, or Firm* — Drinker Biddle & Reath LLP

(57) ABSTRACT

A process for decomposing formates in formate-containing compositions of matter comprises reacting formate-containing compositions of matter in the presence of at least one heterogeneous catalyst comprising lanthanum and at a temperature of from 80 to 180° C. and a pressure of from 0.1 to 60 bar, the formate-containing compositions of matter having a pH of from 6.5 to 10.

10 Claims, No Drawings

METHOD FOR BREAKDOWN OF FORMATES

CROSS-REFERENCE TO RELATED APPLICATIONS

This application is a national stage application (under 35 U.S.C. §371) of PCT/EP2015/054619, filed Mar. 5, 2015, which claims benefit of European Application No. 14159198.2, filed Mar. 12, 2014, both of which are incorporated herein by reference in their entirety.

The invention relates to a process for decomposing formates using a lanthanum-containing catalyst in formate-containing compositions of matter and the use of the catalyst for the aforementioned purpose.

For the purposes of the invention, formate-containing compositions of matter are, in particular, to be understood as meaning compositions of matter comprising carbonyl compounds formed, for example, by an aldol reaction of alkanones or alkanals with formaldehyde, for example methylolalkanals, and also their corresponding hydrogenation products. These products comprise formates well as the aforementioned carbonyl compounds.

The preparation of methylolalkanals and a process for hydrogenation thereof with the aid of a $CuO/Al_2O_3$ catalyst are described in WO 2004/092097 A1.

WO 2011/141470 A1 describes the reaction of isobutyraldehyde with aqueous formaldehyde in the presence of trimethylamine to form hydroxypivalaldehyde (HPA). The reaction effluent comprising HPA is hydrogenated to form neopentyl glycol (NPG) using a hydrogenation catalyst. Lanthanum-containing catalysts are not disclosed.

WO 2007/006719 describes a further process for hydrogenating carbonyl compounds (inter alia aldehydes and hydroxyaldehydes such as hydroxypivalaldehyde), particularly carboxylic acids and their derivatives, wherein the catalyst used is a $CuO/Al_2O_3/La_2O_3$ metal oxide-Cu catalyst. The hydrogenation is generally carried out at a temperature of from 50 to 350° C. and at a pressure of from 3 to 350 bar; the examples were carried out at a pressure of 200 bar at temperatures of 210° C. and 190° C. High conversions and selectivities are achieved. There is no mention of by-product formation.

WO 2011/061185 discloses the use of a supported hydrogenation catalyst, comprising copper as the hydrogenating metal and $Al_2O_3$ and lanthanum oxide as support material and used for hydrogenating carbonyl compounds. The catalyst is pretreated with a base at a pH>10, for example with aqueous sodium hydroxide solution, before it is used in the hydrogenation. The hydrogenation is generally effected at a temperature in the range from 50 to 350° C. and a pressure of from 3 to 350 bar. Examples are shown with hydrogenations conducted at 200° C. and 100° C. and pressures of 200 and 90 bar respectively.

This process has the disadvantage that the selectivity of the hydrogenation of dimethylolbutyraldehyde to form trimethylolpropane decreases by 1-2% as a consequence of the pretreatment of the catalyst with a base. However, no details are provided regarding by-products formed.

Since one of the reactants in the aldolization is formaldehyde, the products formed comprise—in addition to the desired carbonyl compounds—formates owing their existence to formic acid present in the formaldehyde used and/or to Cannizzaro reactions occurring during the reaction with formaldehyde.

These formates can cause disruption in subsequent stages, for example by forming CO during a hydrogenation and/or by esterifying the product, which can lead to yield losses and/or purity issues in the end product. The formates may further liberate formic acid, for example on distillative work-up, which may then lead to undesirable corrosion and necessitates the use of expensive materials of construction.

It is therefore an object of the present invention to provide a process which can be used to completely or at least partially decompose formates present in compositions of matter. It is a further object of the invention that, ideally, no carbon monoxide (CO) is formed on decomposition of the formates.

The invention accordingly provides a process for decomposing formates in formate-containing compositions of matter, which comprises reacting formate-containing compositions of matter in the presence of at least one heterogeneous catalyst comprising lanthanum and at a temperature of from 80 to 180° C. and a pressure of from 0.1 to 60 bar, wherein the formate-containing compositions of matter have a pH of from 6.5 to 10.

For the purposes of the invention, formate-containing compositions of matter are to be understood as meaning, in particular, compositions of matter comprising carbonyl compounds obtained by reactions in the presence of formaldehyde, and/or their corresponding hydrogenation products.

Examples include carbonyl compounds formed by an aldol reaction of alkanones or alkanals with formaldehyde such as, for example, methylolalkanals. The corresponding hydrogenation products thereof can further also be used in the process according to the invention. Hydrogenation products are, in particular, to be understood as meaning those where the aldehyde group or ketone group of the carbonyl compound has been reduced to an alcohol.

The process according to the invention is generally suitable for use before, during or after a hydrogenation of the aforementioned formate-containing compositions of matter. The process according to the invention is preferably used during or after, more preferably during, a hydrogenation.

For the purposes of the present invention, formate is to be understood as meaning formic acid, salts thereof or esters of formic acid with alcohols. These are preferably salts derived from formic acid and amines, preferably from tertiary amines, preferably, for example, trimethylamine, methyldiethylamine, dimethylethylamine, triethylamine. The alkyl component of the amine can also be longer-chained and/or cyclic.

The composition of matter used in accordance with the invention can have a formate content (measured or reckoned as formic acid) of up to 20 000 weight ppm, preferably from 10 to 8000 ppm and more preferably from 100 to 3000 ppm.

The conditions according to the invention decompose the formates present in the composition of matter used according to the invention to an extent of at least 50%, preferably to an extent of at least 70% and more preferably to an extent of at least 80%.

The pH of the formate-containing composition of matter is determined in an aqueous solution comprising at least 50 wt % of water. This means that formate-containing compositions of matter comprising less than 50 wt % of water are appropriately diluted with water to achieve a water content of 50 wt %. When the mixture is not fully miscible, the pH is determined from the aqueous phase. When a formate-containing compositions of matter has a water content of >50%, the pH is determined directly therefrom.

According to the invention, the aqueous solution of the formate-containing composition of matter, the feed solution, has a pH in the range from 6.5 to 10, preferably from 7 to 9.5, more preferably from 7.5 to 9. The determination of the pH is effected in the feed solution before it reaches the catalyst, i.e., before the feed solution comes into contact with the catalyst. When the pH falls below 6.5, the operating life of the catalyst is limited; when the pH is >10, undesired side reactions take place.

The pH is preferably adjusted by metered addition of base. Again, a tertiary amine is preferred. When the formate-containing composition of matter used according to the invention as the feed stream was provided via an aldol reaction in the presence of a tertiary amine, it is particularly preferable to use the same amine for the pH adjustment.

According to the invention, at least one lanthanum-containing catalyst is used in which, preferably, at least some of the lanthanum is present in oxidic form, for example as $La_2O_3$ or in the form of a spinel structure. It is very particularly preferable for at least 30 wt %, based on the total amount of lanthanum present in the catalyst, to be present in oxidic form, for example as $La_2O_3$ or in a spinel structure.

The weight fraction of the lanthanum (reckoned as $La_2O_3$), based on the total weight of the catalyst, is in the range from 0.5% to 85%, preferably in the range from 2% to 60%, more preferably in the range from 3% to 40%, most preferably 4% to 20%, in particular 4% to 15%.

According to the invention, preference is given to lanthanum-containing catalysts further comprising at least copper. The copper can be present as copper oxide (reckoned as CuO) in an amount, based on the total weight of the catalyst, of from 10 to 90 wt %, preferably 20 to 75 wt %, more preferably 30 to 70 wt %, most preferably 40 to 65 wt %. The stated CuO amounts refer to the content prior to activation of the catalyst with hydrogen. At least 99 wt % of the copper oxide can be introduced by precipitation of a soluble precursor such as, for example, $Cu(NO_3)_2$ and at least 1 wt %, preferably at least 2 wt %, more preferably at least 3 wt %, most preferably at least 5 wt % of the CuO, based on the total weight of the catalyst, can be present as pulverulent copper or as copper platelets. Copper introduced in elemental form is converted into copper oxide by calcination in air prior to use of the catalyst.

The lanthanum-containing catalyst used according to the invention can also comprise further materials in addition to copper, for example pulverulent cement, activated carbon or oxidic materials derived from Si, Al, Zr, Ti or mixtures thereof. These materials can be present in the catalyst according to the invention in an amount of 0.5-80 wt %, in each case based on the total weight of the catalyst. Preference is given to carbon, $SiO_2$ and/or $Al_2O_3$, particular preference being given to $Al_2O_3$.

The cement used is preferably a high-alumina cement. It is particularly preferable for the high-alumina cement to consist essentially of aluminum oxide and calcium oxide. It is further possible to use a cement based on magnesium oxide/aluminum oxide, calcium oxide/silicon oxide and calcium oxide/aluminum oxide/iron oxide.

Examples of particularly preferred lanthanum-containing catalysts useful for the process according to the invention, and their methods of preparation, are found in WO 2007/006719 (pages 5-8, 13-14).

According to the invention, very particular preference is given to lanthanum-containing catalysts also capable of hydrogenating carbonyl-containing compounds to form the corresponding alcohols. Examples of catalysts suitable therefor are likewise described in WO 2007/006719 (pages 5-8, 13-14).

Very particular preference is given to lanthanum oxide/copper catalysts, in particular lanthanum oxide/copper/copper oxide catalysts and lanthanum oxide/copper/copper oxide/aluminum oxide catalysts.

Particular preference is given to catalysts comprising or consisting of:
4 to 20 wt % of lanthanum oxide,
30 to 70 wt % of copper oxide,
10 to 30 wt % of aluminum oxide and
3 to 20 wt % of copper,
wherein said materials preferably sum to 100 wt %.

Very particular preference is given to catalysts comprising or consisting of:
4 to 15 wt % of lanthanum oxide,
40 to 65 wt % of copper oxide,
15 to 30 wt % of aluminum oxide and
5 to 20 wt % of copper,
wherein said materials preferably sum to 100 wt %.

The aforementioned makeups of the catalysts refer to the makeup thereof prior to air calcination.

Particularly preferred among the aforementioned catalysts is a catalyst which (prior to air calcination) comprises or consists of:
58 wt % of CuO,
22 wt % of $Al_2O_3$,
5 wt % of $La_2O_3$,
15 wt % of Cu.

The catalyst is generally dried at temperatures of from 50 to 150° C., preferably at 120° C., optionally followed by calcination, preferably in air, preferably for 2 hours, generally at 200 to 600° C., more particularly at 300 to 500° C.

The above-described dried and calcinated catalyst can be subjected to treatment with boiling water and/or steam prior to use in the process according to the invention, to confer high stability on the shaped article used as the catalyst and simultaneously enhance the hydrogenation activity and the selectivity of the catalyst. The water treatment and/or steam treatment of the catalyst can be effected as described in WO 2007/006719 (pages 5 and 6). The treatment is preferably effected with boiling water and/or steam, more preferably with boiling water.

Following the water treatment and/or steam treatment, the catalyst is typically dried again, generally at temperatures of from 50 to 300° C., and optionally calcinated.

The above-described water treatment or steam treatment of the catalyst can be effected before, during or after the hereinbelow described activation of the catalyst.

An aftertreatment of the catalyst with a base solution having a pH of >10, as described in WO 2011/061185, is unsuitable for the process according to the invention and hence explicitly excluded from the scope of protection.

Prior to use, the catalyst used in accordance with the invention is activated with reducing gases such as hydrogen or hydrogen-containing mixtures, preferably with hydrogen, at atmospheric pressure in the range from 20-250° C., more preferably between 100 and 230° C.

The activation of the catalyst can be carried out in the same reactor as the process according to the invention. It is likewise possible to activate the catalyst elsewhere prior to installation into the reactor. It is preferable, following activation, to either cover this catalyst with an inert, liquid substance such as, for example, water or mixtures of water and alcohols such as neopentyl glycol or isobutanol, or to surficially passivate it with, for example, air. In both cases, this catalyst can be used without further activation treatment once installed in the reactor.

The process according to the invention preferably takes place at a temperature in the range from 90 to 150° C., more preferably in the range from 90 to 130° C. The pressure is preferably in the range from 0.5 to 50 bar, more preferably in the range from 0.8 to 45 bar.

The process according to the invention for decomposition of formates can, optionally, also be effected in the presence of hydrogen. When the formate-containing composition of matter is additionally to be hydrogenated during the catalytic reaction, the process according to the invention is generally carried out at a pressure, essentially determined by hydrogen, in the range from 3 to 60 bar, preferably in the range from 5 to 50 bar, more preferably in the range from 8 to 45 bar. The aforementioned pressures are absolute pressures.

The process according to the invention does not generate CO on decomposition of formates, but instead generates $CO_2$ and hydrogen. This hydrogen can be used to hydrogenate carbonyl groups.

Consequently, one advantage of the process according to the invention is that no catalyst deactivation, i.e., poisoning, with CO takes place.

Using the lanthanum-containing catalyst in the manner of the invention for carbonyl hydrogenation as well as for decomposing formates surprisingly results in increased activity and operating life compared to a catalyst not comprising lanthanum.

The lanthanum-containing catalysts used in accordance with the invention are therefore notable for being more active and robust than the corresponding catalysts absent lanthanum, which brings about a longer operating life, as well as for their ability to decompose formates.

The formate-containing compositions of matter used in accordance with the invention comprise, in particular, the reaction effluent from the aldol reaction of an aldehyde having 2 to 24 carbon atoms with formaldehyde as described, for example, in WO 98/28253 A1 and also, further, in WO 2004/092097 A1 and, specifically for isobutyraldehyde, in WO 2011/141470 A1. The aldehyde used in the aldol reaction is generally converted into a methylolalkanal using 1 to 8 times the amount of formaldehyde in the presence of a tertiary amine. The products of the aldol reaction present in the reaction effluent comprise at least one methylol group. In accordance with the invention, the methylolalkanal is preferably hydroxypivalaldehyde or 2,2-bis(hydroxymethyl)butanal. The reaction effluent comprising the methylolalkanal comprises formates as by-product.

The formate-containing composition of matter, in particular the above-described reaction effluent comprising methylolalkanal, is then supplied to the process according to the invention for decomposition of the formates formed.

In a preferred embodiment of the process according to the invention, the methylolalkanal can be hydrogenated simultaneously.

Preferred hydrogenated methylolakanals comprise at least 2 methylol groups. Of particular importance according to the invention are industrially used hydrogenated methylolalkanals such as, for example, neopentyl glycol (NPG) or trimethylolpropane (TMP).

The process according to the invention is generally adjusted to a space velocity over the catalyst (kg of feed/liter of catalyst per hour) of from 0.01 to 100, preferably between 0.05 and 50, more preferably between 0.1 and 30. The feed is generally a mixture composed of alkanal and formate with or without water and with or without alkanol and having a pH of from 6.5 to 10.

The superficial velocity ($m^3$ of feed/$m^2$ of surface area per hour) on continuous operation of the process according to the invention is between 0.1 and 300.

When the process according to the invention is carried out without additional hydrogenation, the superficial velocities are preferably at the lower end of the range, i.e., between 0.1 and 50, preferably between 0.5 and 30. When the process according to the invention is carried out with additional hydrogenation, the superficial velocities are preferably between 10 and 300, more preferably between 10 and 100, since strongly exothermic reactions are often conducted using product recycling for heat removal, at least in a first reactor.

The feed generally comprises water, for example in a wt % range of from 0.5% to 80%, preferably between 1% and 60%, more preferably between 5% and 50%.

Useful reactors include all reactors that are, in principle, suitable for use with solid catalysts. Examples include batch or continuous reactors in which the catalyst is suspended. However, continuous flow reactors where the catalyst is fixedly disposed are preferred, especially when amounts in excess of 50 metric tons per year are to be produced. All industrially useful catalyst geometries can be used, for example tablets, extrudates, trilobes, hollow tablets, etc. The preferred minimum diameter of these shaped bodies is 0.5 mm, 1 mm being particularly preferable.

One reactor can be used, though the use of more than one, disposed in parallel or preferably in series, is also possible.

When a hydrogenation is to be carried out in addition to decomposition of formates according to the invention, it is preferable to use a first reactor with outer liquid circulation with an external heat exchanger, followed by a second reactor operated in straight pass. It is, in principle, immaterial for the formate decomposition whether the reactors are operated in upflow or downflow mode, however the downflow mode is preferred for achieving an improved conversion in the hydrogenation.

The gas generated in the reaction is removed via the flue. Conducting the reaction under pressure causes most of the gas (>80%) to pass into, for example, a so-called pressure separator in which liquid and gas are separated from one another and the gas is decompressed via a pressure regulator. Residual dissolved gas is then normally removed at ambient pressure and also in the subsequent distillation.

The invention further provides for the use of at least one heterogeneous lanthanum-containing catalyst for decomposing formates at a temperature of from 80 to 180° C. and a pressure of from 0.1 to 60 bar in formate-containing compositions of matter having a pH of from 6.5 to 10. The catalyst, the formates, the formate-containing compositions of matter, the pressure and the temperature are as described above.

The process according to the invention is more particularly described in the examples below but is not to be limited thereby.

EXAMPLES

The formate content was in each case determined by ion-exchange chromatography (IC). The $Cu/Al_2O_3$ catalyst was prepared similarly to WO 95/32171 A1, example E; the lanthanum-containing catalyst according to WO 2007/006719 A1, example 2.

The catalysts were activated before use. This involved heating the catalysts to 180° C. under nitrogen at atmospheric pressure and subsequently admixing 10 vol % of hydrogen to the nitrogen stream. After 2 h, the hydrogen content was increased to 100% by 20% per hour in a step-wise fashion.

Example 1 and also the comparative example were carried out as follows:

The catalyst (87 g, 3×3 mm tablets) was activated as described above in a tubular reactor (1) (length 10 m) which was subsequently operated in downflow mode at 40 bar and with temperatures increasing from 98 to 105° C. in the downward direction. The hydrogen flow rate was 10 standard liters (L(STP))/hour. The effluent was collected and, once analyzed, post-hydrogenated at 103° C. and 40 bar in a further reactor (2) over the same activated catalyst (87 g) as in the first reactor.

The formate content of the feed was about 1500 weight ppm.

Feed composition (wt %): about 65% NPG, about 5% hydroxypivalaldehyde, about 25% water, pH 8.1. Other components such as isobutyraldehyde, trimethylamine, methanol, formaldehyde, isobutanol sum to less than 5%.

The results are summarized in Table 1.

NPG-containing bottoms fraction in a distillation. On distillation of the effluents from example 1, the water fraction was found to contain 0.1% of formate in the form of formic acid amine salt and/or NPG formate. On distillation of the effluents from comparative example 1, these were found to contain 1% of formate in the form of formic acid amine salt and/or NPG formate.

Examples 2 and 3

The catalyst (87 g, 3×3 mm tablets) was activated as described above in a tubular reactor (1) (length 10 m) which was subsequently operated in downflow mode at given pressure and temperatures according to table 2. The hydrogen flow rate was 10 L(STP)/hour. The effluent was collected and, once analyzed, posthydrogenated in a further reactor (2) in each case over the same activated catalyst (87 g) as in the first reactor.

The formate content of the feed was about 1500 weight ppm. Feed composition (wt %): about 65% NPG, about 5% hydroxypivalaldehyde, about 25% water, pH 8.1. Other components such as isobutyraldehyde, trimethylamine, methanol, formaldehyde, isobutanol sum to less than 5%. The results are summarized in Table 2.

TABLE 1

| | Catalyst | Space velocity kg of feed/liter of cat × h | Superficial velocity $m^3$ of feed/ $m^2$ × h | Operating time | HPA conversion | Formate content weight ppm |
|---|---|---|---|---|---|---|
| Example 1 | | | | | | |
| Reactor (1) | Similar to | 4.25 | 19 | 1 month | 88% | 1000 |
| Reactor (2) | WO | 0.90 | 4 | | 100% | 200 |
| | 2007/006719 | | | | | |
| Reactor (1) | | 7.0 | 32 | Further 2 | 77% | 1100 |
| Reactor (2) | | 1.5 | 6.5 | months | 100% | 500 |
| Reactor (1) | | 4.25 | 19 | 3 months | 87% | 1000 |
| Reactor (2) | | 0.90 | 4 | +1 week | 100% | 200 |
| Comparative example 1 | | | | | | |
| Reactor (1) | Similar to WO | 4.25 | 19 | 1 month | 85% | 1500 |
| Reactor (2) | 95/32171 | 0.90 | 4 | | 100% | 1300 |
| Reactor (1) | | 7.0 | 32 | Further 2 | 66% | 1500 |
| Reactor (2) | | 1.5 | 6.5 | months | 100% | 1400 |
| Reactor (1) | | 4.25 | 19 | 3 months | 75% | 1500 |
| Reactor (2) | | 0.90 | 4 | +1 week | 100% | 1500 |

It can be seen that after 3 months operating time the catalyst not containing lanthanum (comparative example 1) distinctly deactivated and decomposed almost no formate while the lanthanum-containing catalyst used in the process according to the invention retains excellent activity even after 3 months.

The hydrogenation effluents collected from example 1 and the comparative example, comprising 200 ppm and 1300 ppm of formate respectively, were separated into a predominantly water-containing tops fraction and a predominantly

TABLE 2

| | Catalyst | Space velocity kg of feed/liter of cat × h | Superficial velocity $m^3$ of feed/$m^2$ × h | Pressure bar | T ° C. | HPA conversion | Formate content ppm |
|---|---|---|---|---|---|---|---|
| Example 2 | | | | | | | |
| Reactor (1) | Similar to | 4.25 | 19 | 10 | 98-105 | 65% | 700 |
| Reactor (2) | WO | 0.90 | 4 | 10 | 103 | 100% | 20 |
| | 2007/006719 | | | | | | |
| Example 3 | | | | | | | |
| Reactor (1) | Similar to | 4.25 | 19 | 40 | 120 | 90% | 800 |
| Reactor (2) | WO | 0.90 | 4 | 40 | 120 | 100% | 50 |
| | 2007/006719 | | | | | | |

Example 4

1 kg of the hydrogenation effluents collected from comparative example 1 and comprising about 1500 ppm of formate were reacted with 200 ml of the activated lanthanum-containing catalyst (prepared according to WO 2007/006719 A1, example 2) at 90° C. in a batch experiment. After 30 min, the hydrogenation effluent was found to contain about 250 ppm of formate in the form of formic acid amine salt and/or NPG formate; after 1 hour, 70 ppm of formate were found to remain.

The aforementioned examples show that the process according to the invention is effective in decomposing the formates to an extent of 50% or more.

The invention claimed is:

1. A process for decomposing formates in formate-containing compositions of matter, which comprises reacting formate-containing compositions of matter in the presence of at least one heterogeneous catalyst comprising lanthanum and at a temperature of from 80 to 180° C. and a pressure of from 0.1 to 60 bar,
    wherein the formate-containing compositions of matter have a pH of from 6.5 to 10,
    the catalyst is a lanthanum oxide/copper/copper oxide/aluminum oxide catalyst, comprising 4 to 15 wt % of lanthanum reckoned as $La_2O_3$ and based on the total weight of the catalyst,
    the formate-containing composition of matter comprises carbonyl compounds formed by an aldol reaction of alkanals with formaldehyde and/or their corresponding hydrogenation products, and
    at least 50 wt % of formate is decomposed.

2. The process as claimed in claim 1, wherein the decomposition of the formates is effected in the presence of hydrogen.

3. The process as claimed claim 1, wherein the decomposition of the formates is effected in the presence of a tertiary amine.

4. The process as claimed claim 1, wherein the formate-containing composition of matter comprises compounds comprising at least two methylol groups.

5. The process as claimed in claim 1, wherein the formate-containing composition of matter comprises hydroxypivalaldehyde and neopentyl glycol.

6. The process as claimed in claim 2, wherein the formate-containing composition of matter comprises hydroxypivalaldehyde and neopentyl glycol.

7. The process as claimed in claim 3, wherein the formate-containing composition of matter comprises hydroxypivalaldehyde and neopentyl glycol.

8. The process as claimed in claim 1, wherein the catalyst consists of:
    4 to 15 wt % of lanthanum oxide,
    40 to 65 wt % of copper oxide,
    15 to 30 wt % of aluminum oxide and
    5 to 20 wt % of copper.

9. The process as claimed in claim 6, wherein the catalyst consists of:
    4 to 15 wt % of lanthanum oxide,
    40 to 65 wt % of copper oxide,
    15 to 30 wt % of aluminum oxide and
    5 to 20 wt % of copper.

10. The process as claimed in claim 7, wherein the catalyst consists of:
    4 to 15 wt % of lanthanum oxide,
    40 to 65 wt % of copper oxide,
    15 to 30 wt % of aluminum oxide and
    5 to 20 wt % of copper.

* * * * *